United States Patent [19]

Bowser et al.

[11] Patent Number: 4,824,865
[45] Date of Patent: Apr. 25, 1989

[54] TREATMENT OF SKIN DISORDERS

[75] Inventors: Paul A. Bowser; Richard J. White, both of Wirral, England

[73] Assignee: Lever Brothers Company, New York, N.Y.

[21] Appl. No.: 2,046

[22] Filed: Jan. 12, 1987

[30] Foreign Application Priority Data

Jan. 15, 1986 [GB] United Kingdom ............... 8600822

[51] Int. Cl.$^4$ ............................................. A61K 31/20
[52] U.S. Cl. ................................. 514/558; 514/547; 514/552; 514/858
[58] Field of Search ..................... 514/558, 547, 552

[56] References Cited

U.S. PATENT DOCUMENTS

| | | | |
|---|---|---|---|
| 3,879,537 | 4/1975 | Van Scott et al. | 424/311 |
| 3,920,835 | 11/1975 | Van Scott et al. | 424/311 |
| 3,984,566 | 10/1976 | Van Scott et al. | 424/311 |
| 3,988,470 | 10/1976 | Van Scott et al. | 424/311 |
| 4,021,572 | 5/1977 | Van Scott et al. | 424/311 |
| 4,105,782 | 8/1978 | Yu et al. | 424/311 |
| 4,105,783 | 8/1978 | Yu et al. | 424/311 |
| 4,197,316 | 4/1980 | Yu et al. | 424/311 |
| 4,234,599 | 11/1980 | Van Scott et al. | 424/311 |
| 4,363,815 | 12/1982 | Yu et al. | 424/311 |
| 4,424,234 | 1/1984 | Alderson et al. | 424/317 |
| 4,507,319 | 3/1985 | Barratt et al. | 514/546 |

*Primary Examiner*—Leonard Schenkman
*Attorney, Agent, or Firm*—Milton L. Honig

[57] ABSTRACT

The use of a curative agent chosen from 2-hydroxyoctanoic acid, 2-ketooctanoic acid and certain esters thereof in the preparation of a pharmaceutical composition for the treatment of skin disorders such as Ichthyosiform dermatoses, Conradi's syndrome, Localized hyperkeratotic conditions, Dandruff, Callous forming disorders, Psoriasis, Eczema, Xerosis, Warts, Tinea pedis, Pityriasis, Lichen planus and simplex chronicus, Darier's disease, Pruritus, Seborrhoeic conditions and Scabies.

9 Claims, No Drawings

TREATMENT OF SKIN DISORDERS

FIELD OF INVENTION

The invention relates to the treatment of certain skin disorders, and more particularly to the use of a curative agent chosen from a specific hydroxy acid, keto acid and derivatives thereof in the preparation of pharmaceutical compositions for the treatment of certain specified skin disorders.

BACKGROUND & PRIOR ART

The conventional treatment of skin disorders such as ichthyotic dermatoses, hyperkeratosis and related conditions has included topical application to the affected area of skin of ointments, creams, lotions or powders containing one or more of a wide variety of active ingredients such as organic and inorganic acids, steroids, fungicides, antibiotics and anti-inflammatory substances.

Usually, remission of the disorder is slow and frequently incomplete. Complete remission and cure of some skin conditions can usually only be obtained by the use of potent drugs, such as steroids, having often severe contra indications which limit their widespread use without medical supervision. Also, the topical application of caustic chemicals in the treatment of localised conditions, such as warts, is often accompanied by pain or discomfort which also limits their use.

It has been suggested in the clinical literature that certain skin disorders are due to insufficient acidity in the epidermal acid layer or coat of the skin. Accordingly, certain skin conditions including one reported case of ichthyosis were apparently successfully treated by lowering the pH of the patient's acid coat. The treatment included topical application of a 3% buffered lactic acid-containing cream.

The use of 2-hydroxyoctanoic acid and 2-ketooctanoic acid in the treatment of acne has been reported in U.S. Pat. No. 4,507,319 (Lever Brothers Company). The benefit of treating other skin disorders, such as those referred to hereinbefore, is not contemplated in this reference.

It has also been reported in U.S. Pat. Nos. 3,879,537 3,920,835, 3,984,566, 3,988,470, 4,021,572, 4,105,782, 4,105,783, 4,197,316, 4,234,599 and 4,363,815 (Van Scott and Yu) that a wide variety of skin disorders may be treated successfully by applying topically to the affected skin at least one of several organic acids or esters thereof having from 2 to 6 carbon atoms and having $\alpha$ or $\beta$-carbon functionality. These compounds are reported to include $\alpha$-hydroxy substituted acids and keto acids having $\alpha$-carbon functionality, and their esters. These and other specific acids and/or esters tested by Van Scott and Yu include glycolic acid, citric acid, lactic acid, maleic acid, tartronic acid, tartaric acid, glucuronic acid, pyruvic acid, (including its ethyl and methyl esters), 2-hydroxy isobutyric acid and 3-hydroxy butyric acid.

Extensive testing of these proposals has revealed that although some relief from at least some of the skin disorders reported in the Van Scott and Yu patents has been possible following treatment, complete remission of these disorders has not always been possible, nor is there any evidence that long term freedom from the symptoms of these skin disorders has been experienced when employing the compounds which are the subject of these prior proposals.

It has now been discovered that certain skin disorders may be treated successfully by topical application of a curative agent chosen from the organic acids, 2-hydroxyoctanoic acid, 2-ketooctanoic acid, and certain esters thereof. Comparative testing has shown that not only do these curative agents more rapidly bring about the remission of a wide range of skin disorders than does any of the compounds recommended for this treatment in the prior proposals summarised above, but that this effect is achieved at lower concentrations than the acids and esters specified by Van Scott and Yu. Furthermore, the effective remission of these disorders is far more long lasting. It is also evident that topical application of these curative agents is painless and free from contra indications, provided that the amount employed and their pH of use are kept within defined limits.

It is to be noted that 2-hydroxyoctanoic acid, also known as $\alpha$-hydroxy caprylic acid, 2-ketooctanoic acid and their esters have not been contemplated by Van Scott and Yu as can be seen from a careful study of their patents. It is accordingly all the more surprising that these curative agents should have such a wide spectrum of activity in the successful treatment of skin disorders, the response to treatment following their topical application being far more rapid and dramatic than that of the related $\alpha$-hydroxy organic acids and esters having up to 6 carbon atoms contemplated by Van Scott and Yu.

DEFINITION OF THE INVENTION

Accordingly, the invention provides for the use of a curative agent chosen from 2-hydroxyoctanoic acid, 2 ketooctanoic acid and their $C_2$ to $C_6$ alkyl esters and diglyceride and triglyceride esters, and mixtures thereof, in the preparation of a pharmaceutical composition for the treatment of the skin disorders:
  Ichthyosiform dermatoses, notably:
    Ichthyosis vulgaris,
    Sex-linked ichthyosis,
    Lamellar ichthyosis,
    Epidermolytic ichthyosis,
  Conradi's syndrome
  Localised hyperkeratotic conditions, notably:
    Keratosis pilaris,
    Keratosis punctata,
    Keratosis senilis,
    Keratosis striata,
  Dandruff Callous-forming disorders, notably:
    Palmar and Plantar hyperkeratosis, including corns
    Palmar and Plantar keratoderma
  Psoriasis
  Eczema
  Xerosis
    Warts, notably:
    Keratotic warts,
    Herpes,
    Keratoacanthoma,
  Warty naevus
  Tinea pedis and other dermatomycoses
  Pityriasis rosea & Pityriasis alba
  Lichen planus & Lichen simplex chronicus
  Cicatricial alopecia with dry flaky scalp
  Darier's disease
  Pruritus
  Seborrhoeic dermatitis
  Seborrhoeic eczema Scabies

DISCLOSURE OF THE INVENTION

It is accordingly an object of the invention to provide a pharmaceutical composition containing one or more curative agents as herein defined, which when applied topically to the skin of a person suffering from one or more of the skin disorders, as herein defined, or administered orally or by injection, will alleviate and/or effect remission of the symptoms of the disorder(s).

Particularly preferred curative agents for use in the prepartion of a pharmaceutical composition according the invention are 2-hydroxyoctanoic acid and its $C_2$ to $C_6$ alkyl esters, notably:
  methyl 2-hydroxyoctanoate
  ethyl 2-hydroxyoctanoate
  n-propyl 2-hydroxyoctanoate
  isopropyl 2-hydroxyoctanoate
  n-butyl 2-hydroxyoctanoate
  n-pentyl 2-hydroxyoctanoate
  n-hexyl 2-hydroxyoctanoate
  2-methoxyoctanoic acid
  2-ethoxyoctanoic acid
  2-propoxyoctanoic acid
  methyl 2-methoxyoctanoate
2-ketooctanoic acid and its $C_2$ to $C_6$ alkyl esters, notably:
  methyl 2-ketooctanoate
  ethyl 2-ketooctanoate
The diglycerides and the triglycerides of 2-hydroxyoctanoic acid and 2-ketooctanoic acid.

PREPARATION OF THE PHARMACEUTICAL COMPOSITION

The pharmaceutical composition of the invention can be prepared in the form of a solution, lotion, gel, cream, ointment, solid stick, aerosol or powder, or in other forms suited to administration topically, orally or by injection.

When the pharmaceutical composition is a liquid, such as a lotion or aerosol, or a semi-liquid, such as a gel, cream or ointment, or a solid stick, then it is usually necessary to dissolve an effective quantity of the curative agent in water or ethanol or other aqueous and non-aqueous pharmaceutically acceptable vehicle, and then to admix this solution, if desired, in a conventional manner with a suitable cream or ointment base, or stick base, or with a normally liquefiable gaseous propellant in order to prepare the pharmaceutical composition.

When the pharmaceutical composition is a powder, then it is usually necessary to admix dry, finely divided curative agent with a powder diluent, such as talc, starch, kaolin, Fuller's earth or other suitable powder base in order to provide the pharmaceutical composition in powder form.

The amount of curative agent to be employed in the pharmaceutical compositions of the invention will depend on the nature of the composition. However, it can be stated generally that the amount of the curative agent for this purpose will form from 0.01 to 20%, preferably from 0.5 to 10%, most preferably from 0.5 to 5% by weight of the pharmaceutical composition.

If desired, other pharmaceutically acceptable carriers, diluents or emollients can be incorporated in the pharmaceutical composition according to the invention, in order to facilitate even distribution over the affected area of the skin at a concentration or dosage suitable for treatment of a specific skin disorder.

It is also possible to incorporate in the pharmaceutical composition according to the invention other pharmaceutically active substances, which may further improve the treatment of skin disorders.

Adjustment of pH

When the pharmaceutical composition contains water, then the aqueous phase should have a pH value of from 3 to 6.5, preferably from 3.5 to 5.5 and ideally from 3.5 to 5.0

Although pharmaceutical compositions having a pH value of less than 3 are likey to be effective in the treatment of skin disorders, topical application of such compositions has been found to produce stinging, burning or irritation. Pharmaceutical compositions having a pH value of greater than 6.5 are likely to exhibit reduced effectiveness in the treatment of the skin disorders.

Any suitable pharmaceutically acceptable pH adjustant can be employed to set the pH of the composition at a desired value, provided that precipitation of corresponding curative agent does not occur to any significant degree. Examples of pH adjustants include alkanolamines, especially triethanolamine and buffers such as lactic acid/triethanolamine lactate. Buffers containing sodium ions should preferably be avoided, as precipitation of the corresponding sodium salt, which is less effective in the treatment of skin disorders, can occur.

METHOD OF TREATMENT

The invention also provides a method for the treatment of skin disorders in man and other mammals, namely:
  Ichthyosiform dermatoses, notably:
    Ichthyosis vulgaris
    Sex-linked ichthyosis
    Lamellar ichthyosis
    Epidermolytic ichthyosis
  Conradi's syndrome
  Localized hyperkeratotic conditions, notably:
    Keratosis pilaris
    Keratosis punctata
    Keratosis senilis
    Keratosis striata
  Dandruff
  Callous-forming disorders, notably:
    Palmar and Plantar hyperkeratosis, including corns,
  Palmar and Plantar keratoderma
  Psoriasis
  Eczema
  Xerosis
    Warts, notably:
    Keratotic warts
    Herpes
    Keratoacanthoma
  Warty naevus
  Tinea pedis and other dermatomycoses
  Pityriasis rosea & Pityriasis alba
  Lichen planus & Lichen simplex chronicus
  Cicatricial alopecia with dry flaky scalp
  Darier's disease
  Pruritus
  Seborrhoeic dermatitis
  Seborrhoeic eczema
  Scabies which method of treatment comprises applying to involved areas of the body an effective amount of a composition comprising from 0.01 to 20% by weight of a curative agent selected from the group consisting of 2-hydroxyoctanoic acid, 2-ketooctanoic acid, their $C_2$ to $C_6$ alkyl esters, their diglyceride and triglyceride esters and mixtures thereof; together with a pharmaceutically acceptable vehicle.

EXAMPLES OF THE INVENTION

The following clinical studies illustrate the treatment of skin disorders with pharmaceutical compositions according to the invention.

EXAMPLE 1

This example illustrates the treatment of ichthyosis vulgaris.

20 patients suffering from ichthyosis vulgaris primarily involving the arms, some with atopic eczema, were treated with a cream containing 2% by weight of 2-hydroxyoctanoic acid.

In order to establish superiority of the pharmaceutical composition according to the invention, the clinical test took the form of a comparison with a commercially available product containing 10% by weight of urea, specifically prescribed for the treatment of ichthyosis, hyperkeratosis and other chronic skin conditions. This commercially available product was designated the "contol", whereas the cream containing 2% by weight of 2-hydroxyoctanoic acid (pH 3.8) was the "test" pharmaceutical composition.

The clinical trial was carried out by a consultant dermatologist as a double blind trial, each patient receiving between 1 and 2 g of either the test or control creams twice daily, the cream being applied to the area of the arms affected by this skin disorder.

The clinical study lasted a total of 4 weeks, after which the results were assessed by the consultant dermatologist. It was shown that although the test and the control creams produced an improvement in the condition of the skin of each patient, the affected arms treated with the test cream showed a dramatic and statistically significant improvement over those arms which had been treated with the control cream.

These data clearly demonstrate that the pharmaceutical composition according to the invention containing 2% by weight 2-hydroxyoctanoic acid is superior to a widely used commercially available 10% by weight urea pharmaceutical preparation prescribed for the treatment of ichthyosis, hyperkeratosis and other chronic skin conditions.

EXAMPLE 2

This example illustrates the treatment of dandruff.

Two persons with a long history of severe dandruff were selected for this clinical study. The hair of each subject was shampooed twice with a nonionic shampoo (pH 3.8) containing 2% by weight 2-hydroxyoctanoic acid. The hair in each case was then rinsed with clean water, and the hair dried and set in the normal fashion.

The application of the nonionic shampoo containing 2% by weight 2-hydroxyoctanoic acid was repeated on three successive days employing between 3 to 5 ml of the shampoo at each application.

After the third day, the head of each subject was examined by a trained hairdresser and was found to be free from any evidence of dandruff.

EXAMPLE 3

This example illustrates the treatment of warty naevus.

A child suffering from recalcitrant warty naevi primarily on the abdomen, with some involvement elsewhere on the body, had previously used a variety of treatments for the removal of warty naevi, including 10% by weight salicylic acid, without any observable benefit.

The subject then applied twice daily a cream containing 2% by weight of 2-hydroxyoctanoic acid (pH 3.8) for a period of 20 days.

The warty naevus condition was subsequently examined by a consultant dermatologist, and it was shown that there had been a dramatic improvement in the condition with virtual loss of warty projections.

EXAMPLE 4

This example illustrates the treatment of fungal infection of the foot, specifically tinea pedis.

Two patients suffering from persistent fungal infection of both feet, not responsive to undecenoic acid, applied twice daily a cream containing 2% by weight of 2-hydroxyoctanoic acid (pH 3.8) for a period of seven days.

At the end of this period, the condition had markedly improved, with a return to apparently healthy skin.

EXAMPLE 5

This example illustrates the treatment of an ichthyosiform dermatoses.

A child suffering from Conradi's Syndrome with associated ichthyosiform dermatoses presented having had no response from any topical emollient or keratolytic.

The subject then applied twice daily a cream containing 2% by weight of 2-hydroxyoctanoic acid (pH 3.8) for 3 weeks. This product vastly improved the skin condition reducing the scaling on the arms, legs and trunk to virtually normal.

EXAMPLE 6

This example illustrates the treatment of lamellar ichthyosis.

Two patients suffering from severe lamellar ichthyosis on the abdomen, upper arms and neck ('Dirty Neck Syndrome') presented having had no response to emollients or topical retinoid preparations.

A 2% by weight 2-hydroxyoctanoic acid cream (pH 3.8) was applied for 4 weeks and produced a dramatic reduction in scaling even in the neck region.

EXAMPLE 7

This example illustrates the prevention of Herpes associated cold sores. Two patients suffering from recurrent cold sores presented with early symptoms of cold sores (tingling sensation). Application of a 1% by weight 2-hydroxy octanoic acid cream (pH 4.0) prevented the further onset of the condition.

EXAMPLE 8

This example illustrates the treatment of a psoriasiform condition.

One patient suffering from a recurrent psoriasiform condition on the inner aspects of the arms and legs was diagnosed as suffering from psoriasis inversiform. Previous treatments did not change the condition which was persistent until spontaneous remission. On this current flare, a 1% by weight 2-hydroxyoctanoic acid cream (pH 4.0) was applied to each site, twice a day. At the end of 4 days, the condition dramatically improved and the skin reverted to normal appearance within 1 week.

EXAMPLE 9

This example illustrates the treatment of atopic eczema.

Six children suffering from atopic eczema and ichthyosis vulgaris presented having had little response from topical emollients.

A 2% by weight 2-hydroxyoctanoic acid cream was applied twice daily for 2 weeks, after which considerable resolution of the eczema and ichthyosis had occurred.

EXAMPLE 10

This example illustrates the treatment of keratosis pilaris.

A child suffering from extensive keratosis pilaris on the outer aspects of the upper arms and thighs, unresponsive to salicylic acid or urea preparations, was treated with 2% by weight of 2-hydroxyoctanoic acid (pH 3.8). After 6 weeks of treatment the keratosis pilaris had completely resolved and a smooth skin was apparent.

EXAMPLE 11

This example illustrates the treatment of a clinical manifestation of coarse dry hair of irregular diameter.

An 8 year old girl suffering from a cicatricial alopecia with severely dry flaky scalp washed her hair once every 3 days for 3 weeks with a 2% w/w, 2-hydroxy octanoic acid with 12% non-ionic surfactant. At the end of this, her hair and scalp were much improved for the first time in her life.

What we claim is:

1. A method for the treatment of the skin disorder of *tinea pedis* in man and other mammals, which method of treatment comprises applying to involved areas of the body an effective amount of a composition comprising from 0.01 to 20% by weight of an active agent selected from the group consisting of 2-hydroxyoctanoic acid, 2-ketooctanoic acid, their $C_2$ to $C_6$ alkyl esters, their diglyceride and triglyceride esters and mixtures thereof; together with a pharmaceutically acceptable vehicle.

2. The method of claim 1, wherein the active agent is 2-hyroxyoctanoic acid.

3. The method of claim 2, wherein the composition comprises from 0.5 to 10% by weight of 2-hydroxyoctanoic acid.

4. The method according to claim 2, wherein said composition further comprises an aqueous phase having a pH value of from 3 to 6.5.

5. The method according to claim 2, wherein said composition further comprises an aqueous phase having a pH value of from 3.5 to 5.

6. The method according to claim 2, wherein said composition further comprises a pharmaceutically acceptable non-aqueous vehicle.

7. The method according to claim 6, wherein the non-aqueous vehicle is ethanol.

8. The method according to claim 7, wherein the non-aqueous vehicle is a powder.

9. The method according to claim 2, wherein the composition is in the form of a cream ointment, solid stick or powder.

* * * * *